United States Patent [19]

Steele

[11] Patent Number: 5,139,450

[45] Date of Patent: Aug. 18, 1992

[54] SWIM FIN FOR AN AMPUTEE

[76] Inventor: Gareth E. Steele, 5601 S.W. 1 Ct., Plantation, Fla. 33317

[21] Appl. No.: 524,849

[22] Filed: May 18, 1990

[51] Int. Cl.⁵ .............................................. A63B 31/00
[52] U.S. Cl. ........................................ 441/64; 441/58; D21/239; 36/8.1
[58] Field of Search ........................ 441/55, 56, 58-63; 24/442, 445, 446, 450-452; 36/8.1, 11.5, 116; 446/901; 428/100; 272/18, 71; 52/DIG. 13; 273/DIG. 30; D21/236, 238, 239

[56] References Cited

U.S. PATENT DOCUMENTS

| | | | |
|---|---|---|---|
| 1,494,452 | 5/1924 | Waldron | 441/64 |
| 2,947,010 | 8/1960 | Rabin | 441/59 |
| 3,109,186 | 11/1963 | Glenn | 441/60 |
| 3,239,857 | 3/1966 | Gwynne | 441/64 |
| 3,786,576 | 1/1974 | Russell | 441/59 |
| 3,827,095 | 8/1974 | Feather | 441/59 |
| 3,978,537 | 9/1976 | Shamlian | 441/64 |
| 4,316,300 | 2/1982 | Lewis | 441/59 |
| 4,934,971 | 6/1990 | Picken | 441/64 |
| 4,952,183 | 8/1990 | Gil | 441/64 |

Primary Examiner—Joseph F. Peters, Jr.
Assistant Examiner—Clifford T. Bartz
Attorney, Agent, or Firm—Malloy, Downey & Malloy

[57] ABSTRACT

A swim fin specifically designed for use by an amputee comprising a substantially planar, elongate flipper portion integrally formed with and extending from a receiving pocket adapted to be mounted to the end of a limb of the amputee. A pair of elongate straps are connected along a side of the receiving pocket, wherein the straps are specifically designed to wrap around the amputee's limb, being fastened by a pair of mating hook and loop pads on opposite ends of the straps, thereby effectively securing the swim fin to the amputee's limb.

11 Claims, 1 Drawing Sheet

SWIM FIN FOR AN AMPUTEE

BACKGROUND OF THE INVENTION

1. Field of the Invention

A swim fin specifically designed for attachment to a limb of an amputee for use by the amputee during swimming, and snorkeling.

2. Description of the Prior Art

There are several swim fins, and other water sport related devices to assist handicap people during swimming, diving, snorkeling and other related water activities. Many of these devices are extremely complex and include elaborate harnessing systems which are cumbersome and difficult to adjust and secure to one's body. Other devices in the prior art include a type of prosthesis which has a connective flange with a release mechanism attached at its distal end to which a swim fin can be attached. This type of device is fairly complex and requires extensive tooling making it an extremely expensive, almost impractical device.

In view of the lack of an adequate, simple and inexpensive swim fin which is adapted to be attached to the limb of an amputee, it is almost impossible for an amputee to enjoy the benefits of water sport activities such as scuba diving, snorkeling, and swimming. Without the use of fins, it is extremely difficult for an amputee to generate a propulsive force to move the person through the water as normally required during such activities as scuba diving and swimming Accordingly, there is a need in the water sport industry, and particularly in the area directed to sporting good equipment for the handicap, for a swim fin specifically structured for attachment to the end of a limb of an amputee. Additionally, there is a need in the present art for a swim fin for use by an amputee which is relatively inexpensive to manufacture and simple to attach and detach from the end of the amputee's limb so that an amputee can effectively enjoy water related activities to the same extent as an able bodied person.

SUMMARY OF THE INVENTION

The present invention is directed towards a swim fin specifically structured and configured for attachment to the end of a limb of an amputee. The swim fin of the present invention includes a receiving pocket is formed and configured to fit to the end of an amputee's limb and includes a surrounding side wall structure to partially surround the limb in supporting engagement therewith. A flipper portion, similar to that found on commonly known swim fins, is integrally formed with an extends from the receiving pocket. The flipper portion includes an upper and lower surface extending between two side edges which preferably a reinforce construction to rigidity to the longitudinal construction of the fin. The flipper portion terminates at a distal edge which has a reduced thickness to provide more flexibility as the fin is forced through the water.

A pair of securing straps having an elongate configuration are attached at one end along a side wall of the receiving pocket. To attach the swim fins, the amputee would place the end of the limb through an open end of the fin first sliding receipt within the receiving pocket. To secure the fin thereto, the straps would be wrapped around the limb and fastened in place by means of a mating hook and loop adhesive pads attached at opposite ends of the straps.

The invention accordingly comprises the features of construction, combination of elements, and arrangements of parts which we exemplified in the construction hereinafter set forth and the scope of the invention will be indicated in the claims.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 1:
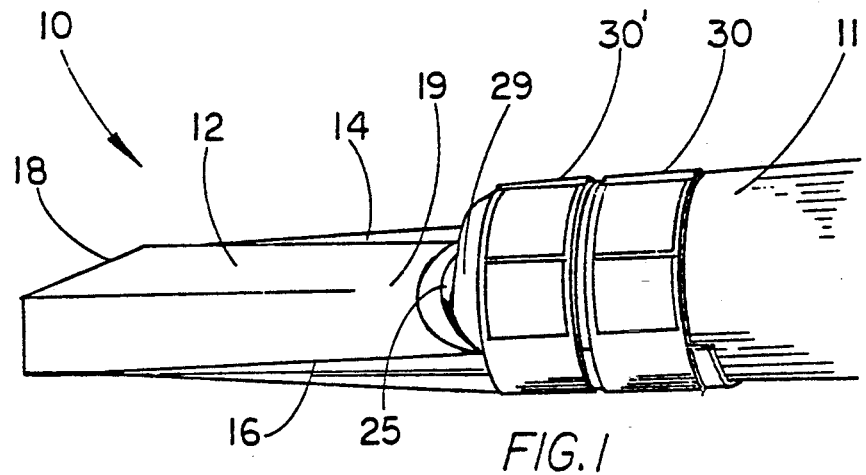
FIG. 1 is a perspective view of the swim fin shown in connection with the limb of an amputee.

As shown in FIGS. 1-4, the present invention relates to a swim fin 10 specifically designed for use by an amputee. As will be explained in greater detail hereinafter, the swim fin is structured and configured so as to fit on the end of a limb of the amputee where it is secured thereto, thus providing a means of propulsion for use in swimming, diving, snorkeling, and other water related activities. With reference to FIG. 1, the swim fin 10 of the present invention includes a generally elongate flipper portion 12 having opposite side edges 14 and 16 and terminating at a distal edge 18. The flipper portion 12 is preferably formed from a substantially flexible yet rigid material sufficient to be flexed during the stroke of one's arm or leg and thereby providing a propulsion force through the water. In a preferred embodiment, the flipper portion 12 is constructed so as to have an area of increased thickness at 19, shown in FIG. 1, wherein the thickness gradually reduces to a minimum thickness at the distal edge 18 in such a manner as to increase the flexibility along the length of the flipper portion to a maximum flexibility at the distal edge 18.

A receiving pocket, generally indicated as 20, is integrally formed with the flipper portion 12 with the flipper portion longitudinally extending from an end thereof, the receiving pocket being specifically configured for receiving attachment to the end of a limb 11 of the user The receiving pocket 20 includes a base 22 extending generally co-planar with a lower surface of the flipper portion 12 and terminating at a proximal edge 23. The receiving pocket 20 further includes a side wall construction extending in perpendicular relation to the base 22 and including opposite side walls 24 and 24' and a curvilinear end wall 25 extending between the side walls 24 and 24'. The receiving pocket 20 is further structured to include an open end as at 26 formed along the proximal edge 23 and specifically adapted and structured for sliding receipt of the swim fin 10 unto the end of the limb 11 such that a swim fin is supported about the end of the limb with the side walls 24 and 24" ported along the sides of a limb 11 and the curvilinear end wall 25 in supporting engagement with a distal end 29 of the limb 11.

Figure 3:
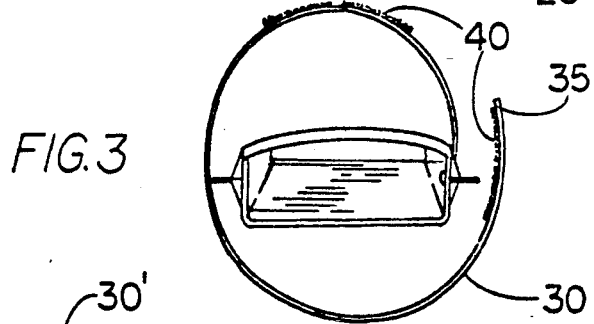
FIG. 3 is an end view of the swim fin of the present invention illustrating the receiving pocket and securing straps.
Figure 4:
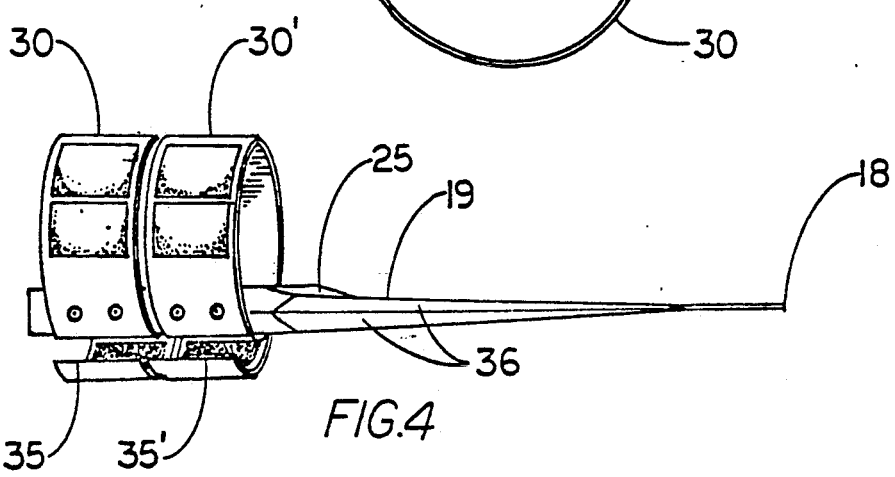
FIG. 4 is a prospective view of the swim fin of the present invention as seen from a side view.

The preferred embodiment includes securing means in the form of a pair of straps 30 and 30' each being connected at one end along the side wall 24 of the receiving pocket 20 whereupon they are adapted to be wrapped around the receiving pocket as illustrated in FIGS. 3 and 4. To secure the swim fin to the limb 11, the straps are wrapped around circumference of the limb with a swim fin in place whereupon the free distal ends 35 and 35'0 of the straps 30, 30' are fastened to the straps by a plurality of mating of hook and loop pads 40 and 40' the plurality of mating hook and loop pads 40 and 40' are disposed along the strap 30, 30' so as to allow the length of the securing portion of the strap 30, 30' to be varied by the positioning of the free distal ends 35 and 35'.

Figure 2:
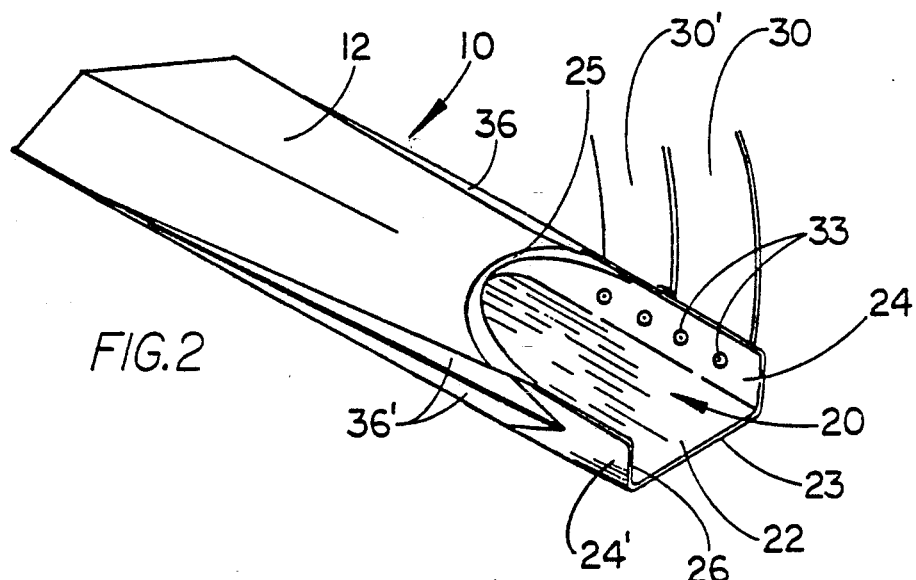
FIG. 2 is a perspective view of the swim fin of the present invention illustrating the receiving pocket.

Referring to FIGS. 2 and 4, the flipper portion 12 in the preferred embodiment includes a reinforced portion 36 and 36' in the form of a vertically extending lip formed on the opposite edges 14 and 16. The reinforced portions 36 and 36' serve to add structural rigidity to the overall structure of the swim fin maintaining it in its generally planar configuration, as shown in FIG. 4.

Now that the invention has been described.

What is claimed is:

1. A swim fin for use by an amputee comprising:
   a) an elongate, substantially planar flipper portion formed of a semi-rigid yet substantially flexible material adapted to provide a propelling force through the water upon flexing, said flipper portion including an upper surface and a lower surface extending between a pair of oppositely disposed side edges, said upper and lower surfaces meeting at a terminal, freely disposed distal edge,
   b) a receiving pocket integrally formed, and extending from said flipper portion opposite from said distal edge, said receiving pocket being structured and configured to adaptively receive a substantially non-flexible, non-tapered limb of the amputee in substantially surrounding, fitting relation thereto,
   c) said receiving pocket being substantially co-planar with said flipper portion so as to position said flipper portion as a co-planar extension of the limb,
   d) securing means for securing and maintaining said swim fin to the limb including at least one elongate strap having one end connected to said swim fin along a side of said receiving pocket and adapted to be wrapped and secured about the limb, thereby maintaining a secure fit of the limb within said receiving pocket, and
   e) said elongate strap being variable in securing length so as to accommodate a range of sizes of both upper and lower limbs of the user.

2. A swim fin as in claim 1 wherein said flipper portion includes a varying degree of thickness along its length, the thickness steadily decreasing to a minimum longitudinal thickness at said distal edge.

3. A swim fin as in claim 2 wherein said flipper portion includes a varying degree of thickness across its width with a maximum transverse thickness being defined along a longitudinal centerline, the thickness steadily decreasing to a minimum thickness defined along said oppositely disposed side edges.

4. A swim fin as in claim 1 wherein said receiving pocket includes a base integrally formed with, and extending from said lower surface of said flipper portion, said base defining a mounting surface for mounting receipt against a side of the user's limb.

5. A swim fin as in claim 4 wherein said receiving pocket includes a substantially surrounding side wall support structure extending upwardly in substantially perpendicular relation to said base being disposed and configured to partially surround the sides end of the limb in supporting, fitting relation thereto.

6. A swim fin as in claim 5 wherein said receiving pocket includes an open end disposed on a proximal end of the swim fin opposite said distal edge, said open end being configured for slidable receipt of the limb into said receiving pocket permitting said base to mate with the side of the limb in supporting relation thereto.

7. A swim fin as in claim 1 wherein said securing means includes a pair of elongate straps, each being attached at one end to a side of the swim fin along said side wall support structure of the receiving pocket, said pair of straps being of a sufficient length to wrap around and surround the limb securing the swim fin thereto.

8. A swim fin as in claim 7 wherein each one of said pair of straps comprises fastening means including a plurality of hook and loop adhering pads attached on opposite surfaces of each of said straps, said hook and loop adhering pads including a first set of pads and a second set of pads being positioned and oriented for mating engagement with said first set of pads to effectively fasten each one of said straps in wrapped, secured position around the limb.

9. A swim fin as in claim 8 wherein the securing length of the straps may be varied by adjusting the positioning of the distal end of said elongate strap with relation to said set of pads.

10. A swim fin as in claim 7 wherein each one of said pair of straps is formed of a rubber material having an adhesive quality sufficient to prevent movement of each one of said straps therein wrapped about the limb in a partially overlapping orientation.

11. A swim fin as in claim 1 wherein said pair of oppositely disposed side edges of said flipper portion include a reinforced structure in the form of a lip extending in perpendicular relation to said upper and lower surfaces along the length of said flipper portion.

* * * * *